United States Patent [19]
Daugherty

[11] Patent Number: 5,542,932
[45] Date of Patent: Aug. 6, 1996

[54] BLOODLESS FLASHBACK VENT

[76] Inventor: Charles W. Daugherty, 3243 E. Little Cottonwood La., Sandy, Utah 84092

[21] Appl. No.: 504,480

[22] Filed: Jul. 20, 1995

[51] Int. Cl.⁶ .................................................. A61M 5/178
[52] U.S. Cl. ........................... 604/168; 604/236; 604/900
[58] Field of Search ..................... 604/168, 900, 604/236, 238, 129

[56] References Cited

U.S. PATENT DOCUMENTS

| | | |
|---|---|---|
| 3,859,998 | 1/1975 | Thomas . |
| 4,046,144 | 9/1977 | McFarlane . |
| 4,193,399 | 3/1980 | Robinson . |
| 4,193,400 | 3/1980 | Loveless et al. . |
| 4,200,096 | 4/1980 | Charvin . |
| 4,207,870 | 6/1980 | Eldridge . |
| 4,365,630 | 12/1982 | McFarlane . |
| 4,682,980 | 7/1987 | Suzuki . |
| 4,894,052 | 1/1990 | Crawford ................................. 604/63 |
| 4,917,671 | 4/1990 | Chang . |
| 5,066,284 | 11/1991 | Mersch et al. ......................... 604/168 |
| 5,226,883 | 6/1993 | Katsaros et al. ....................... 604/110 |
| 5,290,246 | 3/1994 | Yamamoto et al. .................... 604/167 |

*Primary Examiner*—Randall L. Green
*Assistant Examiner*—Perry E. Van Over
*Attorney, Agent, or Firm*—Eric M. Lee, Esq.

[57] ABSTRACT

This invention is an improved flashback vent. A thin piece of biocompatible material is affixed over the open proximal end of a flashback chamber or a plug in the flashback chamber. This material has a plurality of holes formed therein. Thus, where the flashback chamber is used with an IV catheter introducer needle, blood can enter the flashback chamber and allow air to be vented therefrom without blood leaking from the flashback chamber.

12 Claims, 2 Drawing Sheets

BLOODLESS FLASHBACK VENT

BACKGROUND OF THE INVENTION

This invention relates to a vent that can be used for a flashback chamber on a catheter introducer needle assembly.

In order to place an intravenous (IV) catheter into a patient's vein, a hollow introducer needle is used. During the placement of the IV catheter into the vein, it is desirable to determine whether the needle, and hence the IV catheter, have entered the vein. This determination is typically made by the use of a flashback chamber located at the proximal end of the introducer needle. Once the distal tip of the needle enters a patient's vein, blood travels from the distal tip of the needle to the flashback chamber where it collects. Since the flashback chamber is transparent the healthcare worker will be able to observe the blood and know that the catheter entered the vein.

In order for the blood to enter the flashback chamber, air must be vented from the flashback chamber. The quicker the air is vented from the flashback chamber, the quicker the blood can enter the flashback chamber. Unfortunately, if the vent holes provided in the flashback chamber are too large, the blood may be able to leak from the flashback chamber. On the other hand, if the vent holes provided in the flashback chamber are too small, air may not be vented therefrom preventing blood from entering.

Although assemblies have heretofore been provided that plug the flashback chamber yet provide vent holes, they are deficient in that they can be expensive and relatively bulky and require excess material for manufacture and packaging.

SUMMARY OF THE INVENTION

It is therefore an object of the invention to provide a flashback vent for a flashback chamber that allows air to be vented from the flashback chamber but does not leak blood.

It is another object of the invention to provide a flashback vent for a flashback chamber that is inexpensive, relatively small and does not require excess material for manufacture and packaging.

These and other objects are provided by the flashback vent of the invention. A thin film of material having holes formed therein is provided over the open proximal end of a flashback plug. This plug can then be placed over the open proximal end of a flashback chamber. The assembly allows air to be vented from the flashback chamber yet prevents blood from leaking therefrom. Alternatively, the thin film of material could be placed directly over the open proximal end of the flashback chamber obviating the need for a separate plug.

BRIEF DESCRIPTION OF THE DRAWINGS

The above and other objects and advantages will be apparent upon consideration of the following drawings and detailed description. The preferred embodiments of the present invention are illustrated in the appended drawings in which like reference numerals refer to like elements and in which.

DETAILED DESCRIPTION OF THE INVENTION

Figure 1:
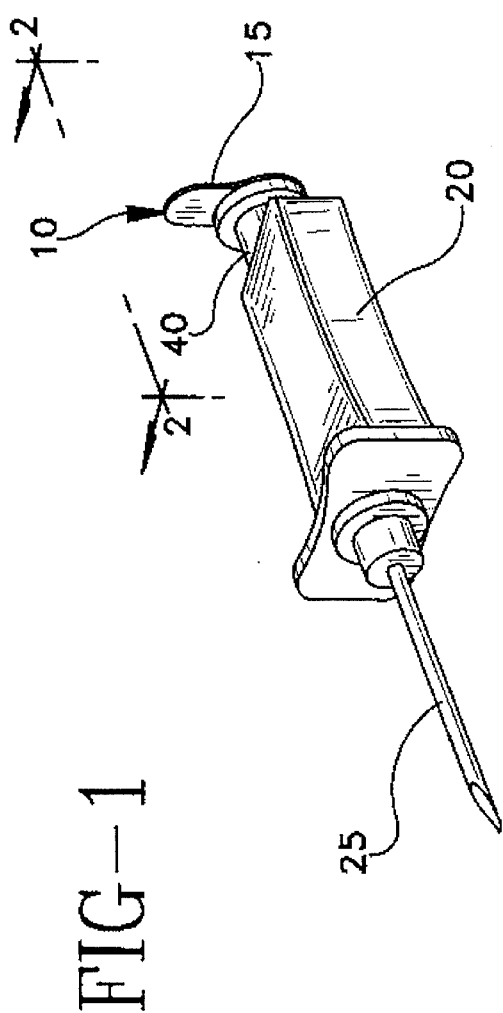
FIG. 1 is a perspective view of an introducer needle assembly incorporating the flashback vent of this invention.
Figure 2:
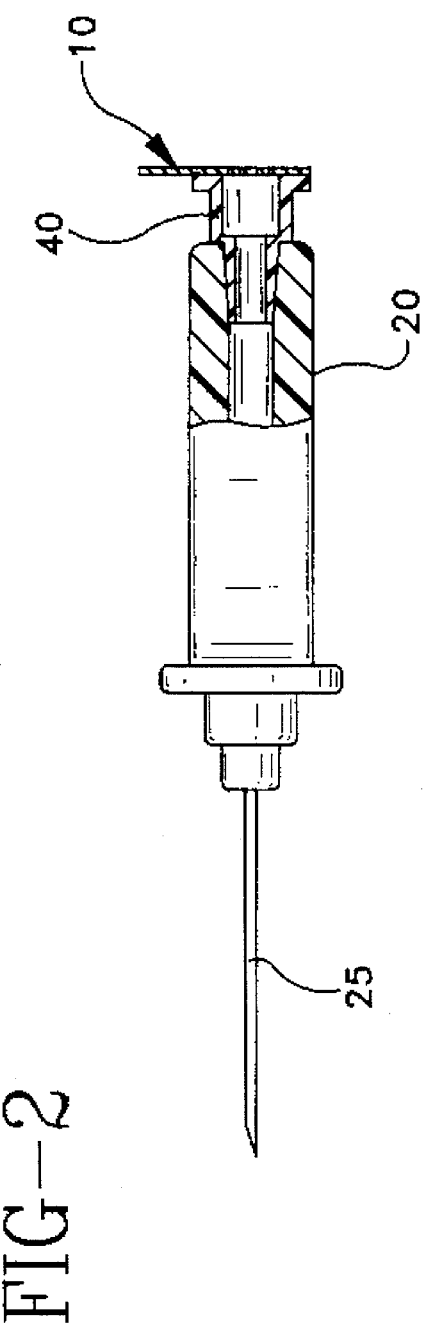
FIG. 2 is a side elevation view partially in section of the introducer needle incorporating the flashback vent of this invention.
Figure 3:
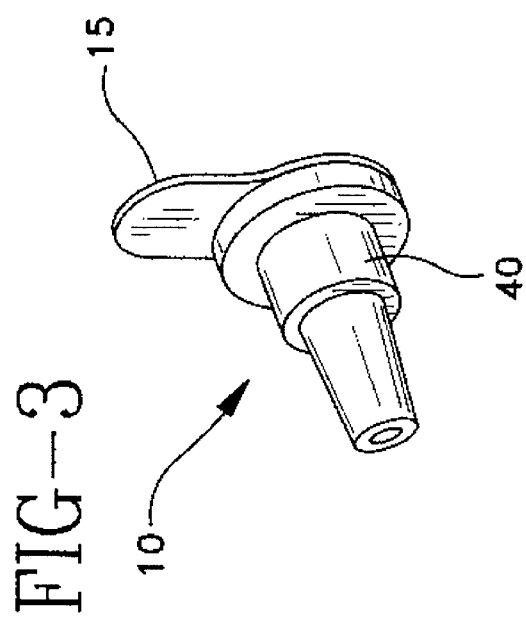
FIG. 3 is a perspective view of a flashback plug incorporating the flashback vent of this invention.
Figure 4:
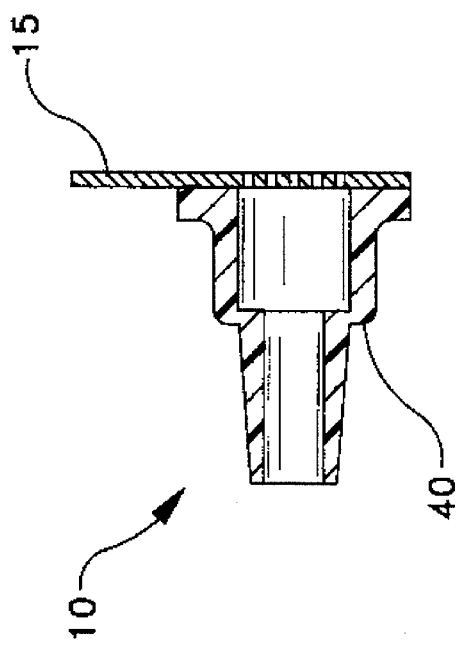
FIG. 4 is a cross-sectional view taken along lines 4—4 of FIG. 3 showing a flashback plug incorporating the flashback vent of this invention.

The flashback vent of this invention is particularly adapted for use with a catheter introducer needle. However, it is to be understood that this invention can be used in any device requiring air to be vented from a chamber to allow liquid to fill the chamber.

As shown in the FIGS., the flashback vent 10 of this invention is located on the open proximal end of a flashback plug 40, which in turn is located at the open proximal end of flashback chamber 20 which in turn is in fluid communication with introducer needle 25. An IV catheter (not shown) can be located over introducer needle 25 prior to insertion into a patient.

Flashback vent 10 can be formed of any biocompatible material that is impervious to blood. For example, a metal foil or plastic could be used. In addition, a peelable filter material, such as a ceramic or a sintered material or a spun bonded polyolefin material such as sold under the TYVEK trademark by E. I. duPont deNemours and Company could be used for vent 10. Vent 10 can be affixed to flashback plug 40 by any standard adhesive method, such as heat sealing, ultrasonic bonding, gluing or spin welding. Preferably vent 10 should have a thickness of between about 0.001 inches to about 0.010 inches. Preferably a tab 15 is formed on vent 10 to facilitate placement or removal of vent 10 from flashback chamber 20.

Figure 5:
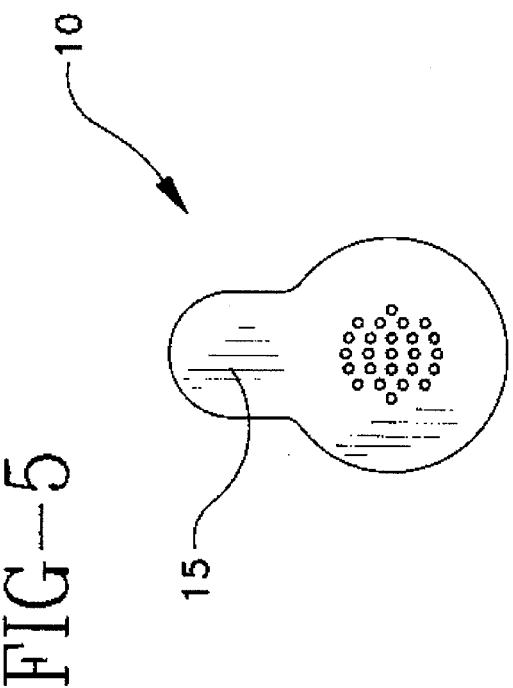
FIG. 5 is an end elevation view of the flashback vent of this invention.

A laser is preferably used to drill holes into vent 10. Preferably an eximer or other ultraviolet light laser is used to drill the holes into vent 10. The holes drilled should have a diameter less than 0.003 inches and greater than 1 micron. Preferably these holes should have a diameter in the range of between 8 and 12 microns although these holes could have a diameter in the range of between 1 and 25 microns. Between 10 and 100 holes can be formed in vent 10. However, with holes having a diameter of between 8 and 12 microns, preferably between 25 to 50 holes should be formed in vent 10. Any arrangement of the holes formed in vent 10 could be used. However, as shown in FIG. 5, the holes should be tightly grouped within a circular boundary to facilitate manufacture.

Although vent 10 is described herein and depicted in the FIGS. as being applied to the open proximal end of a flashback plug 40, vent 10 could also be applied directly to the open proximal end of flashback chamber 20. Flashback plug 40 then would be unnecessary.

Thus it is seen that a flashback vent is provided that vents air from the flashback chamber and seals the open proximal end of the flashback chamber, and that is small, inexpensive, and that does not require excess material for manufacture and packaging.

I claim:

1. An introducer needle assembly, comprising:

a hollow needle having a proximal end and a sharp distal tip;

a flashback chamber defining an interior portion in fluid communication with the hollow needle and having a distal end connected to the proximal end of the hollow needle and further including an opening therein; and a thin, film vent affixed over the opening in the flashback chamber without extending into the interior portion of the flashback chamber, the vent defining a plurality of holes therein.

2. The introducer needle assembly of claim 1 wherein the holes in the vent have a diameter of between 8 microns and 12 microns.

3. The introducer needle assembly of claim 2 wherein between 25 and 50 holes are formed in the vent.

4. The introducer needle assembly of claim 3 wherein the vent is between 0.001 inches and 0.010 inches thick.

5. The introducer needle assembly of claim 1 wherein the vent is a ceramic, sintered or spun bonded polyolefin material.

6. The introducer needle assembly of claim 5 wherein the vent is between 0.001 and 0.010 inches thick.

7. An introducer needle assembly, comprising:

a hollow needle having a proximal end and a sharp distal end;

a flashback chamber in fluid communication with the hollow needle and having an opening therein;

a flashback plug affixed to the opening in the flashback chamber, the flashback plug further defining an interior portion in fluid communication with the flashback chamber and an opening therein; and a thin film vent affixed over the opening in the flashback plug without extending into the interior portion of the flashback plug, the vent defining a plurality of holes therein.

8. The introducer needle assembly of claim 7 wherein the holes in the vent have a diameter of between 8 microns and 12 microns.

9. The introducer needle assembly of claim 8 wherein between 25 and 50 holes are formed in the vent.

10. The introducer needle assembly of claim 9 wherein the vent is between 0.001 inches and 0.010 inches thick.

11. The introducer needle assembly of claim 7 wherein the vent is a ceramic, sintered or spun bonded polyolefin material.

12. The introducer needle assembly of claim 11 wherein the vent is between 0.001 inches and 0.010 inches thick.

* * * * *